(12) United States Patent
Perry et al.

(10) Patent No.: US 7,576,170 B2
(45) Date of Patent: Aug. 18, 2009

(54) CYCLIC SILOXANE COMPOSITIONS FOR THE RELEASE OF ACTIVE INGREDIENTS

(75) Inventors: Robert J. Perry, Niskayuna, NY (US); Mark D. Leatherman, Elmsford, NY (US); Shahid Murtuza, Albany, NY (US)

(73) Assignee: Momentive Performance Materials, Albany, NY (US)

( * ) Notice: Subject to any disclaimer, the term of this patent is extended or adjusted under 35 U.S.C. 154(b) by 993 days.

(21) Appl. No.: 10/742,415

(22) Filed: Dec. 19, 2003

(65) Prior Publication Data

US 2005/0136022 A1 Jun. 23, 2005

(51) Int. Cl.
- C08L 83/06 (2006.01)
- C08L 83/05 (2006.01)
- C08G 77/12 (2006.01)
- C08G 77/14 (2006.01)
- C08G 77/16 (2006.01)

(52) U.S. Cl. ............... 528/37; 528/25; 528/29; 528/31; 528/33

(58) Field of Classification Search .................. None
See application file for complete search history.

(56) References Cited

U.S. PATENT DOCUMENTS

| | | | |
|---|---|---|---|
| 3,215,719 A | 11/1965 | Allen et al. |
| 3,271,305 A | 9/1966 | Allen et al. |
| 4,445,641 A | 5/1984 | Baker et al. |
| 4,500,725 A | 2/1985 | Yemoto et al. |
| 4,524,018 A | 6/1985 | Yemoto et al. |
| 4,908,208 A | 3/1990 | Lee |
| 5,008,115 A | 4/1991 | Lee et al. |
| 5,049,182 A | 9/1991 | Scher et al. |
| 5,071,704 A | 12/1991 | Fischel-Ghodsian |
| 5,130,171 A | 7/1992 | Prud'Homme et al. |
| 5,139,864 A | 8/1992 | Lindauer |
| 5,160,494 A | 11/1992 | Krzysik et al. |
| 5,176,903 A | 1/1993 | Goldberg et al. |
| 5,185,155 A | 2/1993 | Behan et al. |
| 5,213,409 A | 5/1993 | Fisher |
| 5,234,689 A | 8/1993 | Lindauer et al. |
| 5,324,444 A | 6/1994 | Berry et al. |
| 5,372,806 A | 12/1994 | Holloway |
| 5,378,468 A | 1/1995 | Suffis et al. |
| 5,387,411 A | 2/1995 | Abrutyn et al. |
| 5,387,622 A | 2/1995 | Yamamoto |
| 5,449,512 A | 9/1995 | Simmons |
| 5,490,982 A | 2/1996 | Siclliano |
| 5,500,223 A | 3/1996 | Behan et al. |
| 5,525,555 A | 6/1996 | Zank |
| 5,525,588 A | 6/1996 | Michetti |
| 5,587,151 A | 12/1996 | Richard et al. |
| 5,847,179 A | 12/1998 | LeGrow et al. |
| 5,867,755 A | 2/1999 | Sato |
| 6,042,792 A | 3/2000 | Shefer et al. |
| 6,046,156 A | 4/2000 | Perry |
| 6,054,547 A | 4/2000 | Perry et al. |
| 6,063,365 A | 5/2000 | Schefer et al. |
| 6,075,111 A | 6/2000 | Perry et al. |
| 6,077,923 A | 6/2000 | Perry et al. |
| 6,083,901 A | 7/2000 | Perry et al. |
| 6,121,343 A | 9/2000 | Hongo et al. |
| 6,143,309 A | 11/2000 | Legrow et al. |
| 6,153,578 A | 11/2000 | Perry |
| 6,200,949 B1 | 3/2001 | Reijmer et al. |
| 6,228,380 B1 | 5/2001 | LeGrow et al. |
| 6,262,287 B1 | 7/2001 | Anderson et al. |
| 6,267,977 B1 | 7/2001 | LeGrow et al. |
| 6,309,715 B1 | 10/2001 | Lindauer et al. |
| 6,322,777 B1 | 11/2001 | Perry et al. |
| 6,325,274 B2 | 12/2001 | Esumi et al. |
| 6,325,859 B1 | 12/2001 | De Roos et al. |
| 6,435,423 B2 | 8/2002 | Hurry et al. |
| 6,624,136 B2 | 9/2003 | Guerin et al. |
| 2002/0156223 A1 | 10/2002 | Boudjouk et al. |

FOREIGN PATENT DOCUMENTS

| | | | |
|---|---|---|---|
| EP | 106124 A2 | 9/1983 |
| EP | 106124 B1 | 9/1983 |
| EP | 273266 A2 | 12/1987 |
| EP | 273266 A3 | 12/1987 |
| EP | 0334490 A2 | 2/1989 |
| EP | 0334490 A3 | 2/1989 |
| EP | 0334490 B1 | 2/1989 |
| EP | 878497 A2 | 5/1998 |
| EP | 878497 A3 | 5/1998 |
| EP | 0 878 497 A | 11/1998 |
| EP | 0 982 022 A | 3/2000 |
| EP | 0 982 023 A | 3/2000 |
| EP | 0 998 911 A | 5/2000 |

(Continued)

OTHER PUBLICATIONS

Daum, Jeremy et al: "Synthesis and characterization of novel cyclosiloxanes and their self- and co-condensation with silanol-terminated polydimethylsiloxane" Polymer Reprints, vol. 45, No. 2, 2004, pp. 539-540, XP009048491,ISSN: 0032-3934, table 1.

(Continued)

*Primary Examiner*—Michael J Feely
(74) *Attorney, Agent, or Firm*—Kenneth S. Wheelock

(57) ABSTRACT

Cyclic siloxanes that contain releasable active ingredients are described. The active ingredient can be an alcohol or enolizable carbonyl-containing compound such as a ketone, aldehyde, or ester. The product siloxanes are useful in a variety of personal and household care products where slow or controlled release of active ingredient is desired. A preferred embodiment utilizes substituents that when released as active ingredients are fragrant.

21 Claims, No Drawings

FOREIGN PATENT DOCUMENTS

| | | |
|---|---|---|
| EP | 1178107 A2 | 7/2000 |
| EP | 1178107 A3 | 7/2000 |
| EP | 1116515 A2 | 12/2000 |
| EP | 1116515 A3 | 12/2000 |
| EP | 1133929 A1 | 3/2001 |
| GB | 971 309 A | 9/1964 |
| GB | 2041964 A | 1/1980 |
| GB | 2042890 A | 1/1980 |
| JP | 11047581 A | 2/1999 |
| JP | 2002020783 A | 1/2002 |
| WO | WO9628497 A1 | 9/1996 |
| WO | WO9815192 A1 | 4/1998 |
| WO | WO0016643 A1 | 3/2000 |
| WO | WO0016643 A5 | 3/2000 |
| WO | WO0064497 A1 | 11/2000 |
| WO | WO0173188 A1 | 10/2001 |
| WO | WO0179303 A1 | 10/2001 |
| WO | WO0206585 A1 | 1/2002 |
| WO | WO0241709 A1 | 5/2002 |
| WO | WO02076514 A2 | 10/2002 |
| WO | WO02076514 A3 | 10/2002 |
| WO | WO02083620 A1 | 10/2002 |
| WO | WO03032749 A1 | 4/2003 |

OTHER PUBLICATIONS

Database Caplus 'Online! Chemical Abstracts Service< Columbus, Ohio, US; 1988, Kuz'Menko, N. Ya. et al: "Etherification of trichlorophenylsilane and propyl and butyl alcohols", XP0023318909, Database accession No. 1988:75470, compounds under the registry Nos. 112671-14-4, 112671-15-5, 112671-21-3, 11261-22-4, 11267-28-0 & 112671-34-8 abstract—& Voprosky Khimii I Khimicheskoi Tekhnologii, vol. 81, 1986, pp. 79-90, XP009048490 ISSN: 0321-4059.

Sprung M M et al: "The partial hydrolysis of methyltrimethoxysilane" Journal of the American Chemical Society, vol. 77, Aug. 5, 1955, pp. 4173-4175, XP001206395, ISSN: 0002-7863, Compounds II.

Okawara<Rokuro et al: "Alkylalkoxypolysiloxanes. VI. Lower members of cyclic methyl- and ethylethoxypolsiloxanes" Bulletin of the Chemical Society of Japan, vol. 31, No. 1 Jan. 1958, pp. 22-25, XP009048486, ISSN: 0009-2673, table IV.

Okawara, Rokuro et al: "Alkylalkoxypolysiloxanes. VII. Lower members of cyclic methyl- and ethylisopropoxypolsiloxanes" Bulletin of the Chemical Society of Japan, vol. 33, No. 5, May 1960, pp. 659-660, XP009048487, ISSN: 0009-2673, table III.

Andrianov, L. A. et al: "Organic phosphosilicon compounds of sterecyclic structure", Bulletin of the Academy of Sciences of the USSR, Division of Chemical Sciences, vol. 11, 1969, pp. 2300-2306, XP009048488, iSSN: 0568-5230, 7th and 8th entries in table 1.

Crandall J K et al: "Siloxanes from the hydrolysis of isopropyltrimethoxysilane" Jornal of Organometallic Chemistry, vol. 489, No. 1, Mar. 8, 1995, pp. 5-13, XP004024184, ISSN: 0022-328X, Compounds 7, 8 and 13.

CYCLIC SILOXANE COMPOSITIONS FOR THE RELEASE OF ACTIVE INGREDIENTS

CROSS-REFERENCE TO RELATED APPLICATIONS

Not Applicable

STATEMENT REGARDING FEDERALLY FUNDED RESEARCH

Not Applicable

FIELD OF THE INVENTION

The present invention relates to cyclic siloxanes, suitable for use in a variety of applications including personal care formulations, perfumes, household products, detergents, rinse additives, automotive, textiles and molding materials, wherein the cyclic siloxane has been chemically modified to release an active ingredient upon hydrolysis. The present invention further relates to such molecules where the rate of active ingredient release is sufficiently slow so that products formulated with the modified cyclic siloxane exhibit the desired effect for long periods of time.

BACKGROUND OF THE INVENTION

The slow, sustained release of an active ingredient is a highly desirable trait in many personal care, textile, automotive, plastic, laundry and household products. A number of means have been proposed and implemented to achieve this goal. Among these means are dissolving or suspending fragrant compounds in personal care emulsions (U.S. Pat. Nos. 5,525,588; 5,525,555; 5,490,982; 5,372,806; EP 0334490; WO 0064497), encapsulation of a fragrant compound (U.S. Pat. Nos. 5,500,223; 5,324,444; 5,185,155; 5,176,903; 5,130,171; 6,325,859; 6,309,715; 6,325,274; 6,213,409; 6,200,949; 6,042,792; 5,867,755; 5,049,182 6,624,136; U.S. patent applications 20020187221, 20020009522, and 20010008635; EP 1116515, EP 1061124, EP 1133929; WO 0179303, WO 0173188A1, WO 9815192A1, WO 02076514), dissolving a fragrant compound into a hydrophobic phase such as a silicone (U.S. Pat. Nos. 5,449,512; 5,160,494; 5,234,689; WO 0241709A1), incorporation of a fragrant compound into crosslinked polymers (U.S. Pat. Nos. 6,435,423; 5,139,864; 6,379,689; 5,387,622; 5,387,411; WO 03032749; WO 02065858; JP 11047581), incorporation of fragrant compounds into permeable laminates (U.S. Pat. Nos. 6,500,444; 5,071,704; 5,008,115), incorporation of fragrant compounds into matrices that soften at body temperature (U.S. Pat. No. 4,908,208; EP 1178107; WO 0016643), incorporation of fragrant compounds into matrices that biodegrade (U.S. Pat. No. 6,121,343) or are bioactivated (U.S. Pat. No. 5,378,468), incorporation of fragrant compounds into rate controlling membranes (U.S. Pat. Nos. 6,063,365 and 4,445,641), and derivatization of silanes with fragrant alcohols to form alkoxy silanes (U.S. Pat. Nos. 4,524,018 and 4,500,725), derivatization of fragrances to form photosensitive molecules that release the fragrance upon exposure to light (WO 02083620; JP2002020783A). Derivatization of actives to give hydrolyzable organic (i.e., not containing silicon) molecules has also been well documented in the literature.

The marriage of silicon-containing molecules with active ingredients is of particular interest since many active ingredients are highly functional organics and suffer from incompatibility with the silicones that are found in personal and consumer care products, leading to syneresis and other phase separation phenomena. Derivatization of silanes with long-chain alcoholic skin care actives to give alkoxytrimethysilanes (U.S. Pat. No. 5,847,179) and derivatization of silanes with hydroxycarboxylic acid skin exfoliants to form (triorganosilyl)alkoxycarboxylates (U.S. Pat. Nos. 6,143,309; 6,228,380; 6,267,977) have been described. Direct displacement of an alkoxy leaving group on a silicon atom by a fragrant alcohol was reported by Allen, et al. to give fragrant silicon esters or linear silicate esters (U.S. Pat. Nos. 3,215,719 and 3,271,305). Several others also reported similar alkoxy displacement reaction to form linear fragrant siloxane polymers or copolymers (GB 2,041,964; GB 2,042,890; EP 273266). Reaction of an alcohol, aldehyde, ketone or lactone with a silyl hydride in the presence of a metal carboxylate salt and a reducing agent to form linear polymers and copolymers was also reported (WO 9628497). Other routes to fragrant silicones using silyl hydrides were disclosed by Anderson, et al. (EP 878497, JP 10330382, U.S. Pat. No. 6,262,287) and Perry, et al. (U.S. Pat. Nos. 6,046,156; 6,077,923; 6,153,578; 6,054,547; 6,075,111; 6,322,777; 6,083,901). In these processes, hydrosilylation chemistry was employed to join the active portion of the molecule to the silicone backbone. What is not taught or suggested by the prior art is the formation and use of active ingredient-functional cyclic siloxane compositions for personal care, textile, laundry or plastics applications. Herein we disclose a new composition and method for preparation of active ingredient functional cyclic siloxane articles from cyclic silyl hydrides. The method is the direct reaction of an alcohol- or carbonyl-containing compound with the cyclic silyl hydride in the presence of a catalyst to generate the product and hydrogen gas byproduct.

SUMMARY OF THE INVENTION

The present invention provides for an active-releasing cyclic siloxane having formula I or II:

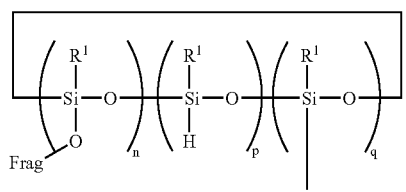
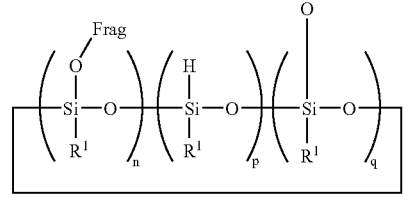

I

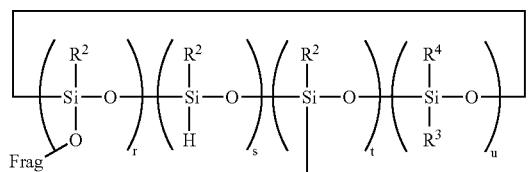
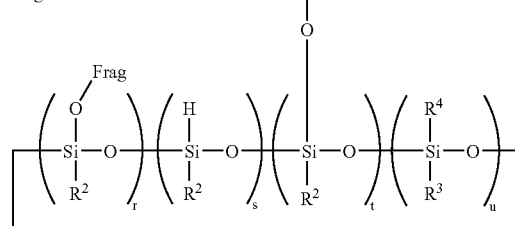

II

For formula I, $R^1$ is hydrogen or a monovalent $C_1$-$C_{24}$ hydrocarbon radical. As used herein, the phrase monovalent hydrocarbon radical includes both aliphatic and aromatic monovalent hydrocarbon radicals that may also include heteroatoms such as oxygen, nitrogen, phosphorous, and sulfur as well as the halogens fluorine, chlorine, bromine, and iodine. The quantity n is at least 1, while the quantities p and q are each independently non-negative with the proviso that the sum n+p+q is greater than or equal to 3. For formula II, $R^2$ is selected from the group consisting of hydrogen or monovalent $C_1$-$C_{24}$ hydrocarbyl radicals. $R^3$ and $R^4$ are each independently hydrogens or a monovalent $C_1$-$C_{24}$ hydrocarbon radicals. The quantities r and u are each independently at least 1, while the quantities s and t are each independently non-negative with the proviso that the sum r+s+t+u is greater than or equal to 3.

The moieties denoted as OFrag are each independently active alkoxide or enolate fragments derived from the alcohol or enolizable carbonyl-containing active ingredient, respectively, wherein Frag is selected from the group consisting of monovalent hydrocarbon radicals having from one to one hundred carbon atoms, preferably four to one hundred carbon atoms, more preferably five to one hundred carbon atoms and most preferably six to one hundred carbon atoms. The present invention also provides for compositions that comprise an active-releasing siloxane. Of particular use are cosmetic compositions that comprise an active-releasing siloxane such as perfumes, skin creams, makeup, foundations and the like, as well as laundry agents such as detergent compositions, rinse additives, fabric softeners and the like.

DETAILED DESCRIPTION OF THE INVENTION

The present invention provides for an active-releasing cyclic siloxane having formula I or II:

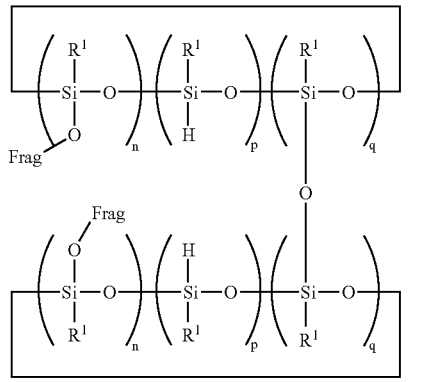

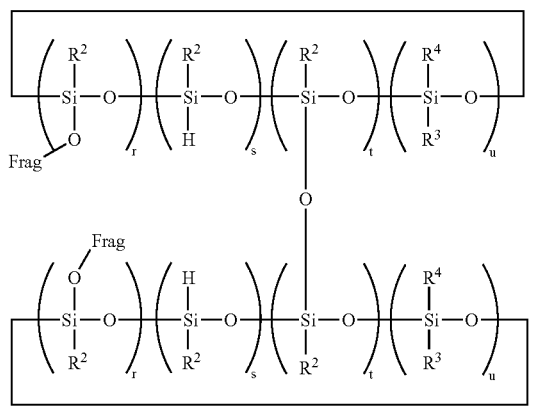

For formula I, $R^1$ is hydrogen or a monovalent $C_1$-$C_{24}$ hydrocarbon radical. As used herein, the phrase monovalent hydrocarbon radical includes both aliphatic and aromatic monovalent hydrocarbon radicals that may also include heteroatoms such as oxygen, nitrogen, phosphorous, and sulfur as well as the-halogens fluorine, chlorine, bromine, and iodine. The quantity n is at least 1, while the quantities p and q are each independently non-negative with the proviso that the sum n+p+q is greater than or equal to 3. For formula II, $R^2$ is selected from the group consisting of hydrogen or monovalent $C_1$-$C_{24}$ hydrocarbyl radicals. $R^3$ and $R^4$ are each independently hydrogens or a monovalent $C_1$-$C_{24}$ hydrocarbon radicals. The quantities r and u are each independently at least 1, while the quantities s and t are each independently non-negative with the proviso that the sum r+s+t+u is greater than or equal to 3.

The moieties denoted as OFrag are each independently active alkoxide or enolate fragments derived from the alcohol or enolizable carbonyl-containing active ingredient, respectively, wherein Frag is selected from the group consisting of monovalent hydrocarbon radicals having from one to one hundred carbon atoms, preferably four to one hundred carbon atoms, more preferably five to one hundred carbon atoms and most preferably six to one hundred carbon atoms. The present invention also provides for compositions that comprise an active-releasing siloxane. Of particular use are cosmetic compositions that comprise an active-releasing siloxane such as perfumes, skin creams, makeup, foundations and the like, as well as laundry agents such as detergent compositions, rinse additives, fabric softeners and the like.

The compounds of the present invention introduce active ingredients via displacement of a hydride from a cyclic silyl hydride. These siloxane molecules are useful in a variety of personal care compositions. The present invention is directed to new compositions of matter that are cyclic siloxanes that release an alcoholic or enolizable carbonyl-containing active ingredient upon hydrolysis, i.e. an alcohol or carbonyl compound releasing siloxane, where the active ingredient can be illustrated by but not limited to adhesion promoters, adhesives, anti-aging agents, antioxidants, antiperspirants, antistatic agents, biocides, bittering agents, bleaching agents, brighteners, colorants, conditioners, defoamers, detergents, disinfectants, dispersing agents, fillers, foaming agents, foam stabilizers, fragrances, humectants, hydrotropes, insect repellants, liquid crystals, moisturizers, odor absorbers, opacifying agents, oral care additives, pharmaceuticals, preservatives, rheology modifiers, screening agents, sequestering or chelating agents, solubilizers, solvents, sunscreens, surfactants, suspending agents, tanning agents, thickeners, vitamins or other nutrients, and whitening agents.

The cyclic hydrido siloxanes utilized by the present invention are described by formula III or IV:

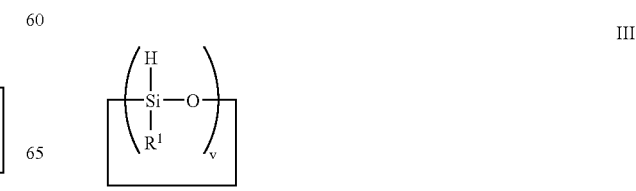

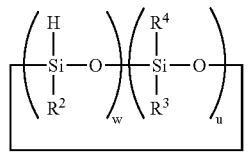

where $R^1$ and $R^2$ are each independently selected from the group consisting of hydrogen or $C_1$-$C_{24}$ monovalent hydrocarbon radicals. The quantity v is greater than or equal to 3, and the quantities w and u are each independently at least 1, with the proviso that w+u must be equal to or greater than 3. $R^3$ and $R^4$ are each independently selected from the group consisting of H or $C_1$-$C_{24}$ monovalent hydrocarbon radicals. The cyclic hydride employed may be a mixture of cyclics of various sizes and concentrations.

The following synthetic examples are intended to illustrate the general synthetic reactions schemes that a person having ordinary skill in the art of siloxane chemistry would typically employ in order to prepare the active-containing cyclic siloxanes used by the present invention. These reaction schemes are thus illustrative only and do not represent the only synthetic pathways that may be utilized.

Reaction scheme I:

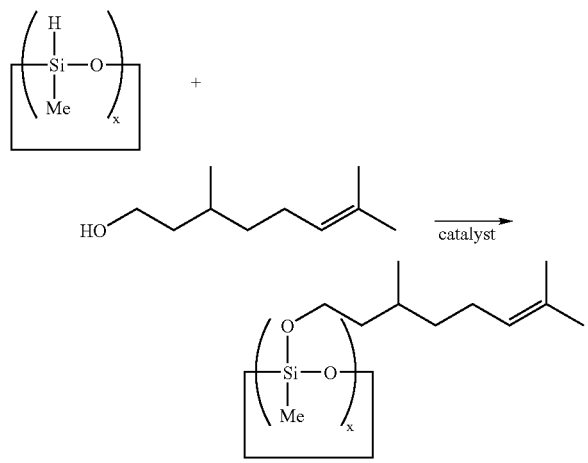

When the starting active ingredient is an alcohol, as depicted in reaction scheme I, the corresponding alkoxysiloxane is produced, preferably in the presence of a suitable catalyst.

Reaction scheme II:

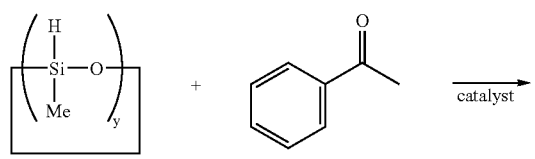

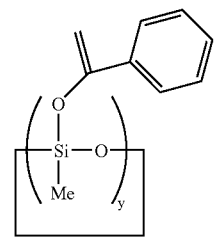

Reaction Scheme III

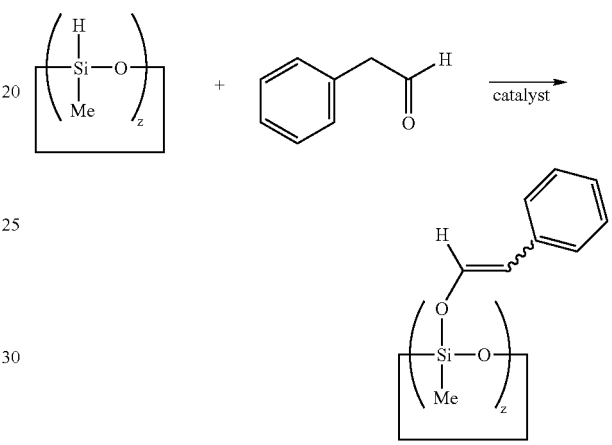

The reaction of a carbonyl-containing active, as depicted in reaction schemes II and III, requires the establishment a carbonyl-enol tautomeric equilibrium, which is assisted by a base such as triethylamine or a silanolate salt.

Tautomerism is the chemical phenomenon of the establishment of an equilibrium between two or more structurally distinct compounds. In nearly all cases, the difference between one tautomeric form of the equilibrium compounds and the other is the isomeric placement of a hydrogen atom. A prevalent form of tautomerism is the tautomeric equilibrium established between a carbonyl compound (i.e. one containing a carbonyl group) and having a hydrogen atom alpha to the carbonyl group, i.e. an a hydrogen:

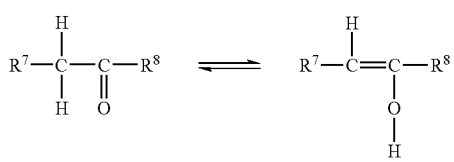

Keto Form          Enol Form

Generally the equilibrium constant favors the keto form and the equilibrium lies well to the left. The extent of enolization is greatly affected by solvent, concentration and temperature. When a strong base is present, both the enol and the keto form can lose a hydrogen ion (a proton), forming an enolate anion:

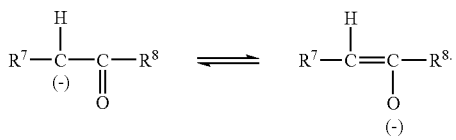

Since both of these structures differ only in the placement of electrons, these are canonical forms of the same ion rather than tautomeric isomers. Because oxygen is more electronegative than carbon, the predominate canonical form is the one where the ionic charge is more localized on the oxygen atom. While the tautomeric equilibrium between enols and ketones or aldehydes is not normally a preparative reaction, the equilibrium must occur since ketones and aldehydes often react through their enol forms as they do instantly in the preparation of the compounds of the present invention. This keto-enol tautomeric equilibrium is also established for esters or organic acids, i.e. in the structures above when $R^8$ includes an oxygen bound to an appropriate R group, e.g. OR', the compound is an organic ester. For a more detailed explanation of this chemistry see J. March "Advanced Organic Chemistry," John Wiley & Sons, New York (1985), pp. 66-68 and 527-529 and references therein.

Fragrant molecules, alcohols, ketones and aldehydes, may be reacted as the alcohol or enol tautomer to produce silicone or siloxanes bearing fragrant moieties. The reaction involves reaction of the alcoholic or enolic form of the molecule with hydrogen, hydroxyl or halogen directly bonded to a silicon atom to form the fragrant derivative. The reaction involves formation of the conjugate base related to the alcohol or enol tautomeric form of the molecule:

FragOH dissociates to $H^+$ and $FragO^-$ (conjugate base); where FragOH is a fragrant alcohol or the enol form of a fragrant ketone or aldehyde. Aldehydes and ketones react with alcohol(s) R'OH to form hemiacetals (derived from aldehydes) or hemiketals (derived from ketones): $RCH(O)+R'OH \rightarrow RCH(OH)(OR')$ hemiacetal, which has a conjugate base obtained by removing the hydroxyl hydrogen: $RCH(O^-)(OR')$ and $RC(O)R''+R'OH \rightarrow RC(OH)(R'O)R''$ which has a conjugate base likewise obtained by removing the hydroxyl hydrogen: $RC(O^-)(R'O)R''$. As used herein the various Frag are fragrant moieties, i.e. monovalent radicals, either as a neutrally charged monovalent radical (Frag or FragO) or as a charged monovalent radical, derived from the conjugate bases of fragrant molecules, e.g. $Frag^+ + O^{-2} \rightarrow FragO^-$, where the monovalent radicals are monovalent hydrocarbon radicals having from one to one hundred carbon atoms, preferably four to one hundred carbon atoms, more preferably five to one hundred carbon atoms and most preferably six to one hundred carbon atoms where the radical may also contain heteroatoms such as oxygen, sulfur, nitrogen, phosphorus and the halogens fluorine, chlorine, bromine and iodine.

While the tautomeric equilibrium between enols and their corresponding carbonyl-containing compounds is not normally a preparative reaction, the equilibrium must occur since carbonyl-containing compounds often react through their enol forms, as they do instantly in the preparation of the compounds of the present invention. As the enol form reacts to give the desired product, more of the carbonyl form tautomerizes to the enol form to maintain equilibrium until the entirety of the carbonyl-containing compound has reacted to give the enol-functionalized siloxane.

The syntheses described above are preferably performed in the presence of a catalyst. For active-containing siloxanes derived from alcohols, several families of catalysts can be used. These include but are not limited to transition metal catalysts, bases, and Lewis acids.

Representative transition metal catalysts that may be used in forming the active-containing cyclic siloxanes of the present invention are illustrated by, but not limited to those that are suitable for hydrosilylation reactions. Many types of platinum catalysts for this reaction (hydrosilation or hydrosilylation) are known, and such platinum catalysts may be used for the reaction in the present instance. The following examples are illustrative and are not intended to limit the scope of catalysts that can be used. The platinum compound can be selected from those having the formula ($PtCl_2$Olefin) and H($PtCl_3$Olefin), as described in U.S. Pat. No. 3,159,601, hereby incorporated by reference. A further platinum-containing material usable in the compositions of the present invention is the cyclopropane complex of platinum chloride described in U.S. Pat. No. 3,159,662, hereby incorporated by reference. Further, the platinum-containing material can be a complex formed from chloroplatinic acid with up to 2 moles per gram of platinum of a member selected from the class consisting of alcohols, ethers, aldehydes and mixtures of the above as described in U.S. Pat. No. 3,220,972, hereby incorporated by reference. The catalysts preferred for use are described in U.S. Pat. Nos. 3,715,334; 3,775,452; and 3,814,730 to Karstedt. Other platinum examples include dipotassium tetrachloroplatinate, platinum metal and platinum halides. Possible rhodium catalysts include but are not limited to tris(dibutylsulfide)rhodium(III)trichloride, chlorotris(triphenylphosphine)rhodium(I), Rh(0), rhodium halides, and complexes of the type $[(diolefin)_2RhCl]_2$ where "diolefin" refers to a diene or two monoalkenes,. Catalysts based on palladium, nickel, rhenium, ruthenium, osmium, copper, cobalt, and iron may also be used. Furthermore, heterogeneous catalysts can be used, whereby catalytic metals or metal complexes such as those mentioned above have been supported on a solid organic or inorganic substance such as silica, alumina, carbon, titania, zirconia, diatomaceous earth, clay, zeolite, or a polymeric substrate. Additional background concerning the art may be found in J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979).

Representative base catalysts that may be used in forming the active-containing cyclic siloxanes of the present invention are illustrated by but not limited to ionic compounds such as hydroxides, siloxane or polysiloxanes containing one or more silanolate groups, amides, alkoxides that possess a lithium, sodium, potassium, rubidium, cesium, magnesium, calcium, strontium, or barium countercation. Nonionic bases such as ammonia and amines can also be used as catalysts.

Representative Lewis acid catalysts that may be used in forming the active-containing cyclic siloxanes of the present invention are illustrated by but not limited to $BF_3$, $FeCl_3$, $AlCl_3$, $ZnCl_2$, $ZnBr_2$, or Lewis acid catalysts of formula (V)

$$MR^9{}_sX_t \qquad (V)$$

wherein M is B, Al, Ga, In or Tl; $R^9$ are independently the same (identical) or different and represent a monovalent aromatic hydrocarbon radical having from 6 to 14 carbon atoms with at least one electron-withdrawing element or group such as —$CF_3$, —$NO_2$ or —CN, or with at least two halogen atoms; X is a halogen atom; s is 1, 2, or 3; and t is 0, 1 or 2; with the proviso that s+t=3, and more preferably a Lewis acid of formula (VI)

$$BR^{10}{}_sX_t \qquad (VI)$$

wherein $R^{10}$ are independently the same (identical) or different and represent a monovalent aromatic hydrocarbon radical having from 6 to 14 carbon atoms with at least one electron-withdrawing element or group such as —$CF_3$, —$NO_2$ or —CN, or with at least two halogen atoms; X is a halogen atom; s is 1, 2, or 3; and t is 0, 1 or 2; with the proviso that s+t=3, most preferably $B(C_6F_5)_3$.

It should be noted that while the starting cyclic silicone hydrides are generally unbranched molecules, hydrolysis before reaction of the active ingredient or after formation of the active-containing siloxane can lead to branched structures, as delineated by subscripts q and t in formulas I and II, respectively.

Representative alcohols that may be used in forming the active-containing cyclic siloxanes of the present invention are illustrated by, but not limited to acetovanillone, allyl amylglycolate, allyl isoamylglycolate, α-amylcinammyl alcohol, anisyl alcohol, benzoin, benzyl alcohol, benzyl salicylate, 1-butanol, butylated hydroxytoluene, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose petaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, 6-isoascorbic acid, isoborneol, isoeugenol, isophytol, isopropyl alcohol, p-isopropylbenzyl alcohol, 4-isopropylcylcohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyl ethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, β-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycols, polysorbate 20, polysorbate 60, polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringealdehyde, α-terpineol, tetrahydrogeraniol, tetrahydrolinalool, tetrahydromyrcenol, thymol, triethyl citrate, 1,2,6-trihydroxyhexane, p-α,α-trimethylbenzyl alcohol, 2-(5,5,6-trimethylbicyclo[2.2.1]hept-2-ylcyclohexanol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose.

Representative carbonyl-containing actives or carbonyl active ingredients that may be used in forming the fragrant cyclic siloxanes of the present invention are illustrated by, but not limited to 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bornyl acetate, bornyl isovalerate, bornyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthalide, butyl 2-methylbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro-nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethylphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3-epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate, ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexalactone, γ-hexalactone, 3-hexenyl acetate, cis-3-hexenyl 2-methylbutanoate, cis-3-hexenyl cis-3-hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methybutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobornyl acetate, isobornyl propionate, isobutyl acetate, isobutyl butyrate, isobutyl cinnamate, isobutyl hexanoate, isobutyl isobutyrate, isobutyl 2-methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-(1-propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutyl isovalerate, 3-methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3-(4-t-butylphenylpropylidene) anthranilate, methyl (methylthio)acetate, methyl 2-(methylthio) propionate, methyl myristate, methyl nonanoate, methyl octanoate, methyl palmitate, 4-(4-methyl-3-pentenyl)-3-cyclohexenylmethyl acetate, methyl 2-methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3-phenylpropan-2-yl acetate, methyl 3-phenylpropionate, methyl propionate, 2-methylpropyl phenylacetate, methyl phenylacetate, 2-methyl-3-phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate, δ-nonalactone, γ-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, octyl butyrate, octyl isobutyrate, octyl isovalerate, octyl octanoate, octyl propionate, oxacycloheptadec-10-en-2-one, ω-pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropionate, phenethyl octanoate, phenethyl phenylacetate, phenethyl propionate, phenoxyethyl propionate, 2-phenoxyethyl 2-methylpropionate, 3-phenyl-2-propenyl propionate, 3-phenylpropyl acetate, 2-phenylpropyl butyrate, 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, δ-nonalactone, tetrahydrofurfuryl acetate, tetrahydrofurfuryl butyrate, tetrahydrofurfuryl propionate, tetrahydrolinalyl acetate, 2,6,6,8-tetramethyl-tricyclo[5.3.1.0(1.5)]udecan-8-yl acetate, p-tolyl acetate, p-tolyl isobutyrate, p-tolyl phenylacetate, triacetin, tributyl acetylcitrate, tributyrin, tripropionin, 3,5,5-trimethylhexyl acetate, δ-undecalactone, γ-undecalactone, γ-valerolactone, vanillin acetate, vanillyl isobutyrate, 1-vinyl-2-(1-methylpropyl)cyclohexyl acetate, and whiskey lactone.

Representative carbonyl-containing actives that may also be used in forming the fragrant cyclic siloxanes of the present invention are illustrated by but not limited to butyraldehyde, citronellal, decanal, cis-4-decenal, trans-4-decenal, 2,4-dimethyl-3-cyclohexen-1-carbaldehyde, 2,6-dimethyl-5-heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3-(p-isopropylphenyl)propionaldehyde, isovaleraldehyde, lauric aldehyde, 2-methylbutyraldehyde, 2-methyl-3-(p-isopropylphenyl)propionaldehyde, 2-methylpentanal, 4-(4-methyl-3-pentenyl)-3-cyclohexen-1-carbaldehyde, 4-methylphenylacetaldehyde, 3-(methylthio)butanal, 2-methyl-4-(2,6,6-trimethyl-2-cyclohexen-1-yl)butanal, 2-methylundecanal, nonanal, cis-6-nonenal, octanal, phenylacetaldehyde, 2-phenylpropionaldehyde, 3-phenylpropionaldehyde, propionaldehyde, p-tolylacetaldehyde, tridecanal, 2,4,6-trimethyl-3-cyclohexen-1-carbaldehyde, 2,6,10-trimethyl-9-undecanal, 7-undecenal, 8-undecenal, 9-undecenal, 10-undecenal, and valeraldehyde.

Representative carbonyl-containing actives that may also be used in forming the fragrant cyclic siloxanes of the present invention are illustrated by but not limited to acetanisole, 1'-acetonaphthone, 2'-acetonaphthone, acetone, acetophenone, 2-acetoxy-2,5-dimethyl-3(2H)furanone, 2-acetylcyclopentanone, 4-acetyl-1,1-dimethyl-6-t-butylindan, 7-acetyl-1,1,3,4,4,6-hexamethylindan, 2-acetyl-2-thiazoline, 6-acetyl-1,1,2,4,4,7-hexamethyl tetralin, allyl α-ionone, benzylideneacetone, 2,3-butanedione, 2-sec-butylcyclohexanone, 5-t-butyl-3,5-dinitro-2,6-dimethylacetophenone, butyrophenone, camphor, 2-decanone, 3-decanone, 3-decen-2-one, dihydrocarvone, dihydro-p-ionone, dihydrojasmone, 4,5-dihydro-3(2H)-thiophenone, 2',4'-dimethylacetophenone, 3,4-dimethyl-1,2-cyclopentadione, 3,5-dimethyl-1,2-cyclopentadione, 2,6-dimethyl-4-heptanone, 1,3-diphenyl-2- propanone, 4-(1-ethoxyvinyl)-3,3,5,5-tetramethylcyclohexanone, p-ethylacetophenone, ethyl vinyl ketone, geranylacetone, 2,3-heptanedione, 2-heptanone, 3-heptanone, 4-heptanone, 3,4-hexanedione, 3-hexanone, 4-hexen-3-one, 2-hexylidene cyclopentanone, α-ionone, β-ionone, 4-isobutyl-2,6-dimethyl-3,5-dinitroacetophenone, isophorone, 6-isopropyldecahydro-2-naphthone, cis-jasmone, livescone, 4-methoxyacetophenone, 4-(p-methoxyphenyl)-2-butanone, 4'-methylacetophenone, 3-methyl-1,2-cyclohexanedione, 3-methyl-2-cyclohexen-1-one, 2-(2-(4-methyl-3-cylcohexen-1-yl)propyl)cyclopentanone, 3-methyl-2-cyclopenten-1-one, methyl dihydrojasmonate, methyl ethyl ketone, 2-methyl-3-heptanone, 5-methyl-2-hepten-4-one, 6-methyl-5-hepten-2-one, 5-methyl-cα-ionone, 1-(2-methyl-5-isopropyl-2-cyclohexenyl)-1-propanone, 4-methyl-2-pentanone, 3-methyl-2-(2-pentenyl)-2-cyclopenten-1-one, 4-methyl-1-phenyl-2-pentanone, 2-methyltetrahydrofuran-3-one, 2-methyltetrahydrothiophen-3-one, 2-nonanone, 3-nonanone, 2-octanone, 3-octanone, 1-octen-3-one, 3-octen-2-one, 4-oxoisophorone, 2-pentadecanone, 2,3-pentanedione, 2-pentanone, 3-pentanone, 3-penten-2-one, 1-phenyl-1,2-propandione, propiophenone, pulegone, 2-tridecanone, 2,2,6-trimethylcyclohexanone, 4-(2,6,6-trimethyl-2-cylcohexen-1-yl)-3-methyl-3-buten-2-one, 2-undecanone, and 6-undecanone.

The active-releasing siloxanes of the present invention are prepared via displacement of a hydride from a cyclic silyl hydride. Thus an organohydrogen siloxane having formula III or IV:

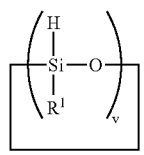

III

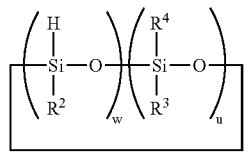

IV where $R^1$ and $R^2$ are each independently selected from the group consisting of hydrogen or $C_1$-$C_{24}$ monovalent hydrocarbon radicals. The quantity v is greater than or equal to 3, and the quantities w and u are each independently at least 1, with the proviso that w+u must be equal to or greater than 3. $R^3$ and $R^4$ are each independently selected from the group consisting of H or $C_1$-$C_{24}$ monovalent hydrocarbon radicals. The cyclic hydride employed may be a mixture of cyclics of various sizes and concentrations.

The cyclic silicone hydride is reacted under conditions as outlined above to produce an active-releasing siloxane having formula I or II:

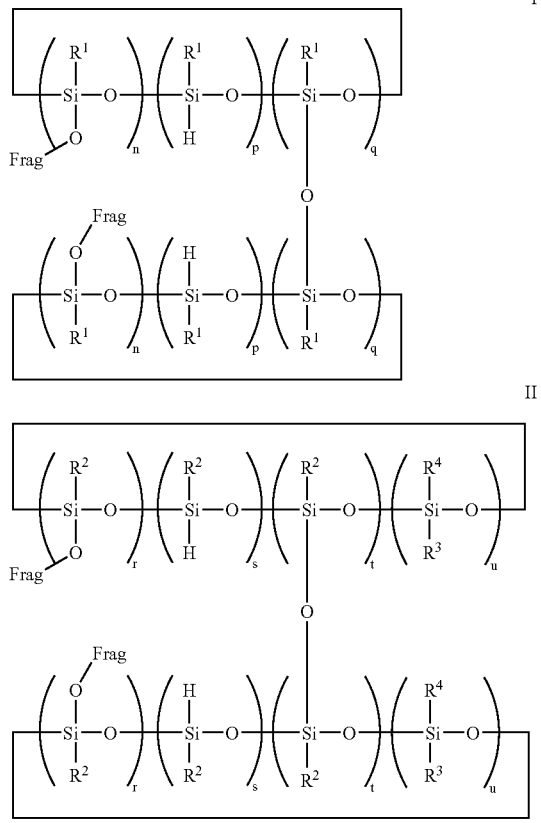

where the components and subscripts satisfy the previous definitions and requirements. This siloxane undergoes a slow hydrolysis under most conditions of use whereby the siloxane releases an active ingredient upon hydrolysis. This imparts a desirable effect to many different useful compositions such as cosmetics and household products.

The active-releasing compounds of the present invention are particularly suited to incorporation into personal care products to impart a long-lasting, desirable effect to the products. Suitable uses include but are not limited to deodorants; antiperspirants; skin creams; facial creams; hair care products such as shampoos, mousses, and styling gels; insect repellants; protective creams; shaving creams; after shave; cologne; perfume; color cosmetics such as lipsticks, foundations, blushes, makeup, and mascara; and other cosmetic formulations where other silicon containing components may have been added and where a certain effect is desired.

Incorporation of small amounts of the compositions of the present invention into fragrance products such as shaving lotions, colognes, toilet water, and perfumes can impart a desirable long lasting fragrance to these products. Further, the fragrant cyclic siloxanes of the present invention may be incorporated into other products where it is desirable to mask unpleasant odors with a pleasant fragrance, for example household cleaning products such as waxes and polishes, automobile cleaning products such as waxes and polishes, detergents, textile coatings, paints, and varnishes.

In addition, the active-containing cyclic siloxanes of the present invention may be used in laundry applications such as rinse additives, softeners and the like, subject to the limitation that the active-containing cyclic siloxanes of the present invention be compatible or capable of being rendered compatible with the product in which it is incorporated.

Experimental

EXAMPLE 1

Citronellol (5.89 g, 0.038 mol) and a mixture of cyclic silicone hydrides (2.0 g, 0.033 mol) were added together, mixed and treated with potassium silanolate-functionalized silicone (0.02 g, 0.015 mmol). After stirring for 15 min, the solution was heated to 60° C. for 18 h. Volatiles were removed by vacuum stripping at 80° C./6 mn Hg for 1 h to give product (6.5 g, 91%).

EXAMPLE 2

A mixture of cyclic silicone hydrides (6.50 g, 0.108 mol hydride) was charged to a roundbottom flask. Citronellol (18.58 g, 0.119 mol) and a 10.9% solution of Pt(0) in divinyltetramethylsiloxane (28.9 mg of solution, 126 ppm Pt) were miscibilized and added dropwise to the hydride over 45 min. Gas evolution was observed. The flask was then heated to 70° C. for 68 h, after which volatiles were removed from the pale brown solution by vacuum stripping at 70° C./2 mm Hg for 3 h to give 22.77 g product (98%).

EXAMPLE 3

A mixture of cyclic silicone hydrides (7.75 g, 0.129 mol hydride) was charged to a roundbottom flask, which was heated to 70° C. Phenethyl alcohol (17.32 g, 0.142 mol) and a 10.9% solution of Pt(0) in divinyltetramethylsiloxane (6.7 mg of solution, 29 ppm Pt) were miscibilized and added dropwise to the hydride over 2 h. Gas evolution was observed. The pale yellow solution stirred at 70° C. for 5.5 d, after which volatiles were removed from the solution by vacuum stripping at 80° C./1 mm Hg for 4 h to give 23.14 g product (99.5%).

EXAMPLE 4

In a roundbottom flask, tris(pentafluorophenyl)borane (42.7 mg, 83.4 µmol) was dissolved in eugenol (15.04 g, 0.092 mol) to give a bright yellow solution. A mixture of cyclic silicone hydrides (5 g, 0.083 mol hydride) was added dropwise, clouding the solution. The addition was complete in 7 min, giving a milky mixture. After 30 min of stirring, gas evolution was observed, and the mixture cleared to give a pale yellow solution which stirred at ambient temperature for a total of 14.5 h. Volatiles were removed under vacuum at 70° C./0.1 mm Hg for 5 h. The mixture was filtered, yielding 17.89 pale yellow liquid (97%).

EXAMPLE 5

In a roundbottom flask, 2-isopropylphenol (13.94 g, 0.102 mol) and tris(pentafluorophenylborane) (0.052 g, 101 µmol) were stirred for 15 min, giving a pale green-yellow solution. A mixture of cyclic silicone hydrides (6.23 g, 0.102 mol hydride) was added dropwise over 1 h. Hydrogen gas evolution was observed during the addition. The solution was stirred for 40 min at ambient temperature, then at 50° C. for 2.5 h. Volatiles were removed under vacuum at 70° C. (3 mm Hg) for 1.5 h, yielding 16.5 g (82.5%).

EXAMPLE 6

In a roundbottom flask, phenethyl alcohol (6.74 g, 0.055 mol) and a 1.36% Rh solution of ("Bu$_2$S)$_3$RhCl$_3$ in ethanol (42 mg of solution, 100 ppm Rh) were stirred together at ambient temperature. A mixture of cyclic silicone hydrides (3.37 g, 0.055 mol hydride) was added dropwise over 75 min and stirred for an additional 75 min. The solution was heated to 70° C., at which gas evolution was observed. After stirring at 70° C. for 18.5 h, the solution was dark gray-green. The flask was cooled to ambient temperature, and the volatiles were removed under vacuum at 70° C./1.2 mm Hg for 1.5 h. The product was filtered to give 7.65 g product (76.5%).

EXAMPLE 7

In a roundbottom flask, citronellol (7.26 g, 0.046 mol) and a 1.36% Rh solution of ("Bu$_2$S)$_3$RhCl$_3$ in ethanol (35 mg of solution, 100 ppm Rh) were stirred together at ambient temperature. A mixture of cyclic silicone hydrides (2.83 g, 0.046 mol hydride) was added dropwise over 55 min. The solution was heated to 70° C.; gas evolution was observed within minutes. After stirring at 70° C. for 40 h, the flask was cooled to ambient temperature, and the volatiles were removed under vacuum at 70° C./1-2 mm Hg for 1 h. The product was filtered to give 7.85 g of dark gray fluid (78.5%).

EXAMPLE 8

In a roundbottom flask, acetophenone (6.74 g, 0.056 mol) and 4.3% KOH-equivalent potassium silanolate-functional silicone (0.073 g, 56 µmol) were dissolved in 15 mL toluene at ambient temperature. The pure cyclic silicone hydride 1,3,5,7-tetramethycyclotetrasiloxane (3.37 g, 0.056 mol hydride) was added dropwise over 30 min. Gas evolution was observed. Following the addition, the solution stirred at ambient temperature for 2 h. The solution was then heated to 70° C. and stirred for 2 h. Volatiles were removed at 70° C./5 mm Hg for 1.5 h. The product was filtered to give 8.30 g of pale orange fluid (83%).

EXAMPLE 9

In a roundbottom flask, hexanal (6.33 g, 0.063 mol), toluene (15 g), triethylamine (0.012 g, 0.126 mmol), and a 10.9% solution of Pt(0) in divinyltetramethylsiloxane (17 mg of solution, 150 ppm Pt) were stirred for 10 min at ambient temperature. The pure cyclic silicone hydride 1,3,5,7-tetramethylcyclotetrasiloxane was added dropwise over 15 min. Gas evolution was observed, and the mixture was heated to and held at 70° C. for 24 h, after which an another charge of the 10.9% solution of Pt(0) in divinyltetramethylsiloxane (17 mg of solution added, 300 ppm Pt total) was added. The mixture was stirred another 12 h at 70° C. then stripped at 70° C./3 mm Hg for 1.5 h to give a maroon fluid 8.3 g of maroon fluid (83%).

EXAMPLES 10-14

Hydrolysis of Products From Examples 2,4,5,6, and 8, Respectively

The general procedure for hydrolysis is as follows:

A solution of the active ingredient-functional silicone (1.0 g), tetrahydrofuran (10 g), and bibenzyl internal standard (0.4 g) was prepared. The solution was analyzed by gas chromatography, then 0.50 mL of 1% (wt.) aqueous sodium hydroxide solution was added (except for example 9, in which 0.125 mL of 1% aqueous sodium hydroxide solution was used). The mixture was stirred and periodically sampled for gas chromatography analysis. Tables 1-5 demonstrate the release profiles determined in examples 10-14, respectively.

TABLE 1

Hydrolysis of product from Example 2.

| Time (h) | Relative citronellol concentration |
|---|---|
| 0.05 | 0.303 |
| 5.25 | 0.432 |
| 21.00 | 0.583 |
| 29.58 | 0.621 |
| 37.76 | 0.662 |
| 45.66 | 0.663 |
| 54.11 | 0.696 |
| 78.05 | 0.723 |
| 144.77 | 0.757 |
| 219.80 | 0.749 |

TABLE 2

Hydrolysis of product from Example 4.

| Time (h) | Relative eugenol concentration |
|---|---|
| 0.00 | 0.238 |
| 1.58 | 1.154 |
| 6.17 | 1.169 |
| 22.50 | 1.163 |
| 47.00 | 1.189 |

TABLE 3

Hydrolysis of product from Example 5.

| Time (h) | Relative 2-isopropylphenol concentration |
|---|---|
| 0.00 | 0.163 |
| 0.92 | 1.316 |
| 5.50 | 1.351 |
| 21.83 | 1.335 |
| 46.33 | 1.352 |

TABLE 4

Hydrolysis of product from Example 6.

| Time (h) | Relative phenethyl alcohol concentration |
|---|---|
| 0.00 | 0.230 |
| 2.25 | 0.958 |
| 6.83 | 1.205 |
| 23.17 | 1.300 |
| 27.33 | 1.226 |
| 49.66 | 1.302 |

TABLE 5

Hydrolysis of product from Example 8.

| Time (h) | Relative acetophenone concentration |
|---|---|
| 0.00 | 0.311 |
| 2.25 | 0.448 |
| 5.75 | 0.532 |
| 20.66 | 0.899 |

TABLE 5-continued

Hydrolysis of product from Example 8.

| Time (h) | Relative acetophenone concentration |
|---|---|
| 27.17 | 0.921 |
| 49.75 | 1.121 |
| 71.66 | 1.156 |
| 140.92 | 1.202 |

EXAMPLES 15 and 16

Hydrolysis of Products From Examples 3 and 8, Respectively

The general procedure for hydrolysis is as follows:
A 3.3 cm by 3.3 cm swatch of untreated cotton cloth was soaked with each material such that the molar equivalents of active ingredient were equal between all of the samples. Each swatch was kept in a small aluminum pan, and all of the pans were kept in an open-top box in the same room at ambient temperature and humidity. The samples were smelled at timed intervals and rated for strength of scent (0=no scent, 5=same strength as pure active ingredient from the bottle). Data are presented in Tables 6 and 7. In both examples 15 (Table 6) and 16 (Table 7), it can be seen that the cloth treated with the siloxane derivative of the present invention release a stronger odor for a longer period of time.

TABLE 6

Relative odor of fabric swatches (Example 15).

| Hours | Control | Siloxane from Ex. 3 |
|---|---|---|
| 0 | 5 | 4 |
| 5 | 4 | 4 |
| 21.5 | 4 | 4 |
| 28.9 | 3 | 4 |
| 46.3 | 3 | 3 |
| 52.8 | 3 | 4 |
| 78.1 | 3 | 4 |
| 164.3 | 3 | 2 |
| 215.3 | 2 | 3 |
| 237.1 | 1 | 1 |

TABLE 7

Relative odor of fabric swatches (Example 16).

| Hours | Control | Siloxane from Ex. 8 |
|---|---|---|
| 0.0 | 5 | 4 |
| 4.7 | 4 | 4 |
| 21.1 | 4 | 3 |
| 28.6 | 1 | 3 |
| 46.0 | 1 | 1 |
| 52.6 | 0 | 1 |
| 77.8 | 0 | 1 |
| 164.0 | 0 | 1 |
| 215.1 | 0 | 1 |
| 236.8 | 0 | 1 |

What is claimed is:
1. An alcohol or carbonyl compound releasing siloxane selected from the group of siloxanes consisting of siloxanes having the formulas

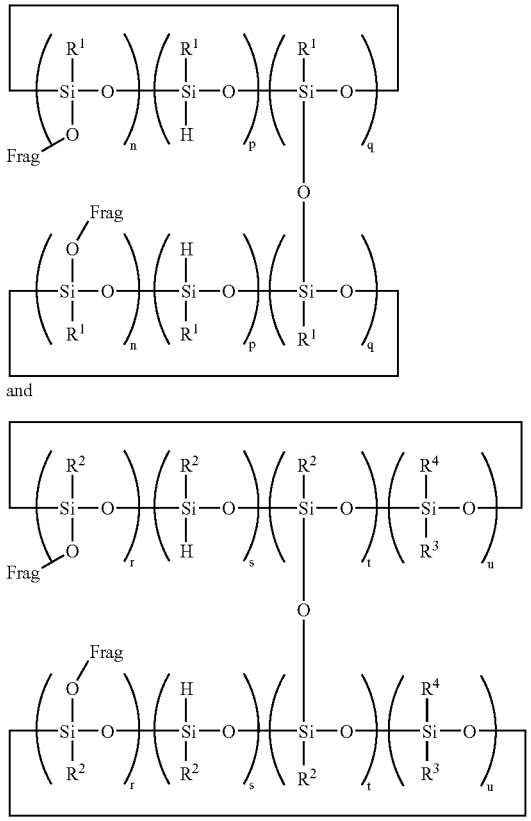

where $R^1$ and $R^2$ are independently hydrogen or monovalent $C_1$-$C_{24}$ hydrocarbon radical, the subscript n is at least 1 or greater, while the subscripts p and q are independently positive subject to the limitation that n+p+q is greater than or equal to 3; $R^3$ and $R^4$ are each independently hydrogen or a monovalent $C_1$-$C_{24}$ hydrocarbon radicals; the subscripts r and u are each independently at least 1 or greater, while the subscripts s and t are each independently positive subject to the limitation that the sum r+s+t+u is greater than or equal to 4; and O-Frag is independently active alkoxide or enolate moieties derived from corresponding active alcohols or carbonyl-containing compounds.

2. The alcohol or carbonyl compound releasing siloxane of claim 1 having the formula:

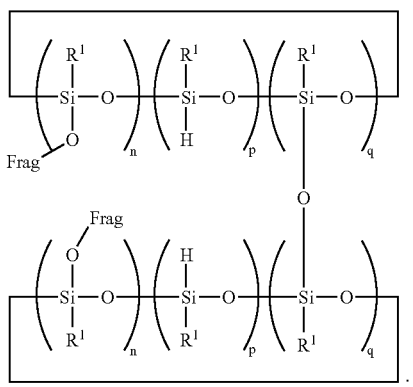

3. The alcohol or carbonyl compound releasing siloxane of claim 2 wherein said siloxane releases an alcohol.

4. The siloxane of claim 3 wherein the alcohol released is selected from the group of fragrant alcohols consisting of acetovanillone, allyl amylglycolate, allyl isoamylglycolate, α-amylcinammyl alcohol, anisyl alcohol, benzoin, benzyl alcohol, benzyl salicylate, 1-butanol, butylated hydroxytoluene, butyl lactate, 2-t-butyl-5 methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyt-2,6-octadien-1-ol, 3,7-dimethyl-l,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glycerol, glyceryl monostearate, guaiacol, 1-heptanol, 2-heptanol, 3-heptanol, cis-4-heptenol, cis-3-heptenol, n-hexanol, 2-hexanol, 3 -hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellol, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, 6-isoascorbic acid, isobomeol, isoeugenol, isophytol, isopropyl alcohol, p-isopropylbenzyl alcohol, 4-isopropylcylcohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyt ethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen- 1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, β-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-i-pentanol, phytol, pinacol, polyalkylene glycols, polysorbate 20, polysorbate 60, polysorbate 80, prenol, n -propanol, propenyl guaethol, propylene glycol, 2-propyiphenol, 4-propyiphenol, resorcinol, retinol, salicylaldehyde, sorbitan monostearate, sorbitol, stearyl alcohol, syringealdehyde, α-terpineol, tetrahydrogeraniol, tetrahydrolinalool, tetrahydromyrcenol, thymol, triethyl citrate, 1,2, 6-trihydroxyhexane, p-α,α-trimethylbenzyl alcohol, 2-(5,5, 6-trimethylbicyclo [2.2.1]hept-2-ylcyclohexmlol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose.

5. A composition comprising the siloxane of claim 3.

6. The alcohol or carbonyl compound releasing siloxane of claim 2 wherein said siloxane releases a carbonyl compound.

7. The siloxane of claim 6 wherein the carbonyl compound released is selected from the group consisting of glucose pentaacetate, 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bomyl acetate, bomyl isovalerate, bomyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthatide, butyl 2-methytbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro-nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethyiphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3-epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate, ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexalactone, γ-hexalactone, 3-hexenyl acetate, cis-3-hexenyl 2-methylbutanoate, cis-3-hexenyl cis-3- hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methybutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobomyl acetate, isobornyl propionate, isobutyl acetate, isobutyl butyrate, isobutyl cinnamate, isobutyl hexanoate, isobutyl isobutyrate, isobutyl 2-methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-( 1 -propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutyti isovalerate, 3 -methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3 - (4-t-butylphenylpropylidene) anthranilate, methyl (methylthio)acetate, methyl 2-(methylthio) propionate, methyl myristate, methyl nonanoate, methyl octanoate, methyl palmitate, 4-(4-methyl-3 -pentenyl)-3 -cyclohexenylmethyl acetate, methyl 2- methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3 -phenylpropan-2-yl acetate, methyl 3 -phenylpropionate, methyl propionate, 2-methyipropyl phenylacetate, methyl phenylacetate, 2-methyl-3 -phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate,δ-nonalactone, γ-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, octyl butyrate, octyl isobutyrate, octyl isovalerate, octyl octanoate, octyl propionate, oxacycloheptadec-10-en-2-one, ω -pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropanoate, phenethyl octanoate, phenethyl phenylacetate, phenethyl propionate, phenoxyethyl propionate, 2-phenoxyethyl 2-methylpropionate, 3 -phenyl-2-propenyl propionate, 3-phenylpropyl acetate, 2-phenylpropyl butyrate, 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, δ-nonalactone, tetrahydrofurfuryl acetate, tetrahydrofurfuryl butyrate, tetrahydrofurfuryl propionate, tetrahydrolinalyl acetate, 2,6,6,8-tetramethyl-tricyclo [5.3.10 (1.5)]udecan-8-yl acetate, p-tolyl acetate, p-tolyl isobutyrate, p-tolyl phenylacetate, triacetin, tributyl acetylcitrate, tributyrin, tripropionin, 3,5,5 -trimethylhexyl acetate, δ-undecalactone, γ-undecalactone, γ-valerolactone, vanillin acetate, vanillyl isobutyrate, 1 -vinyl-2-( 1 -methylpropyl)cyclohexyl acetate, whiskey lactone, butyraldehyde, citronellal, decanal, cis-4-decenal, trans-4-decenal, 2,4-dimethyl-3 -cyclohexen-l-carbaldehyde, 2,6-dimethyl-5 -heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3 -(p-isopropylphenyl) propionaldehyde, isovaleraldehyde, laurie aldehyde, 2-methylbutyraldehyde, 2-methyl-3-(p -isopropylphenyl)propionaldehyde, 2-methylpentanal, 4-(4-methyl-3 -pentenyl)-3 -cyclohexen- 1 -carbaldehyde, 4-methyiphenylacetaldehyde, 3 -(methylthio)butanal, 2-methyl4-(2,6,6-trimethyl-2-cyclohexen- 1 -yl)butanal, 2-methylundecanal, nonanal, cis-6-nonenal, octanal, phenylacetaldehyde, 2-phenyipropionaldehyde, 3 -phenyipropionaldehyde, propionaldehyde, p-tolylacetaldehyde, tridecanal, 2,4,6-trimethyl-3 -cyclohexen-l-carbatdehyde, 2,6,10-trimethyl-9-undecanal, 7-undecenal, 8-undecenal, 9-undecenal, 10-undecenal, valeraldehyde, acetanisole, 1'-acetonaphthone, 2'-acetonaphthone, acetone, acetophenone, 2-acetoxy-2,5 -dimethyl -3(2H)furanone, 2-acetylcyclopentanone, 4-acetyl-1,1-dimethyl-6-t-butylindan, 7-acetyl-1,1, 3,4,4,6-hexamethylindan, 2-acetyl-2-thiazoline, 6-acetyl- 1,1,2,4,4,7-hexamethyl tetralin, allyl α-ionone, benzylideneacetone, 2,3 -butanedione, 2-sec-butylcyclohexanone, 5 -t-butyl-3,5 -dinitro-2,6-dimethylacetophenone, butyrophenone, camphor, 2-decanone, 3 -decanone, 3 -decen-2-one, dihydrocarvone, dihydro-p-ionone, dihydrojasmone, 4,5 -dihydro-3 (2H)-thiophenone, 2',4' -dimethytacetophenone, 3,4- dimethyl-1, 2-cyclopentadione, 3,5 -dimethyl-1,2-cyclopentadione, 2,6-dimethyl-4-heptanone, 1,3 -diphenyl-2-propanone, 4-(1-ethoxyvinyl)-3,3,5,5 -tetramethylcyclohexanone, p-ethylacetophenone, ethyl vinyl ketone, geranylacetone, 2,3 -heptanedione, 2-heptanone, 3 -heptanone, 4-heptanone, 3,4-hexanedione, 3-hexanone, 4-hexen-3 -one, 2-hexylidene cyclopentanone, a-ionone, b-ionone, 4-isobutyt-2,6-dimethyl- 3,5-dinitroacetophenone, isophorone, 6-isopropyldecahydro-2-naphthone, cis-j asmone, livescone, 4-methoxyacetophenone, 4-(p-methoxyphenyl)-2-butanone, 4'-methylacetophenone, 3-methyl -1,2-cyclohexanedione, 3-methyl-2-cyclohexen-1-one, 2-(2-(4-methyl-3 -cylcohexen- 1-yl) propyl)cyclopentanone, 3 -methyl-2-cyclopenten-_1-one, methyl dihydroj asmonate, methyl ethyl ketone, 2-methyl-3 -heptanone, 5 -methyl-2- hepten-4-one, 6-methyl-S -hepten-2-one, 5-methyl-α -ionone, 1 -(2-methyl-S -isopropyl-2-cyclohexenyl)-1-propanone, 4-methyl-2-pentanone, 3-methyl -2-(2-pentenyl)-2-cyctopenten-1-one, 4-methyl-1-phenyl-2-pentanone, 2-methyltetrahydrofuran -3-one, 2-methyltetrahydrothiophen-3 -one, 2-nonanone, 3 -nonanone, 2-octanone, 3 -octanone, 1-octen-3 -one, 3 -octen-2-one, 4-oxoisophorone, 2-pentadecanone, 2,3 -pentanedione, 2-pentanone, 3 -pentanone, 3-penten-2-one, 1 -phenyl-1,2-propandione, propiophenone, pulegone, 2-tridecanone, 2,2,6-trimethylcyclohexanone, 4-(2,6,6-trimethyl-2-cyleohexen- 1 -yl)-3 -methyl-3 -buten-2-one, 2-undecanorte, and 6-undecanone.

8. A composition comprising the siloxane of claim 6.

9. A composition comprising the siloxane of claim 2.

10. The alcohol or carbonyl compound releasing siloxane of claim 1 having the formula:

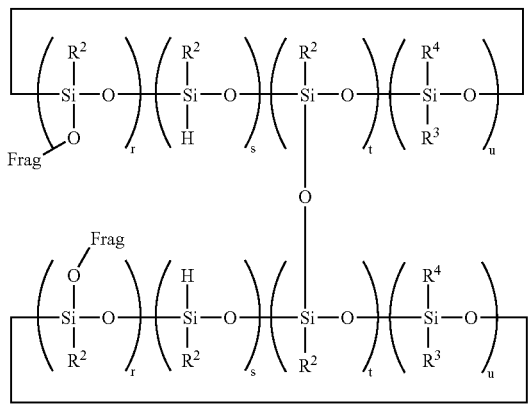

11. The alcohol or carbonyl compound releasing siloxane of claim 10 wherein said siloxane releases an alcohol.

12. The siloxane of claim 11 wherein the alcohol released is selected from the group of fragrant alcohols consisting of acetovanillone, allyl amylglycolate, allyl isoamylglycolate, α-amylcinammyl alcohol, anisyl alcohol, benzoin, benzyl alcohol, benzyl salicylate, 1-butanol, butylated hydroxytoluene, butyl lactate, 2-t-butyl-5 methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyt-2,6-octadien- 1 -ol, 3,7dimethyl-1, 6-octadein,-3-ol, 3,7-dimethyl- 1 -octanol, 3,7-dimethyl-3-octanol, 3,7-dimethyl-6-octen- 1 -ol, 3,7-dimethyl-7-octen- 1 -ol, dimetol, 2-ethylfenchol, 4-ethylguaiacol, 2-ethyl-1-hexanol, ethyl 2-hydroxybenzoate, ethyl 3-hydroxybutyrate, 3 -ethyl-2-hydroxy-2-cyclopenten- 1-one, ethyl 2-hydroxycaproate, ethyl 3-hydroxyhexanoate, ethyl lactate, ethyl maltol, p-ethylphenol, ethyl salicylate, eugenol, famesol, fenchyl alcohol, geraniol, glycerol, glyceryl monostearate, guaiacol, 1-heptanol, 2-heptanol, 3-heptanol, cis-4-heptenol, cis-3 -heptenol, n-hexanol, 2-hexanol, 3 -hexanol, cis-2-hexenol, cis-3 -hexenol, trans-3-hexenol, 4-hexenol, cis-3-hexenyl hydrocinnamyl alcohol, 2- hydroxybenzoate, 2-hydroxyacetophenone, 4-hydroxybenzyl alcohol, 3 hydroxy-2- butanone, hydroxycitronellol, 4-(4-hydroxy-3 -methoxyphenyl)-2-butanone, 2-hydroxy-3 -methyl-2-cyclopenten- 1-one, 4-(p -hydroxyphenyl)-2-butanone, 2-hydroxy-3,5,5 -trimethyl-2-cyclohexenone, 6-isoascorbic acid, isobomeol, isoeugenol, isophytol, isopropyl alcohol, p-isopropylbenzyl alcohol, 4-isopropylcylcohexanol, 3 -isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4- vinylphenol, cc-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7 dimethyl-7-hydroxyoctylideneanthranilate, methyl 3-hydroxyhexanoate, 6-methyl-5 hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyt ethyl)-3,4 dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-l-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, β3-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-i-pentanol, phytol, pinacol, polyalkylene glycols, polysorbate 20, polysorbate 60, polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringealdehyde, α-terpineol, tetrahydrogeraniol, tetrahydrolinalool, tetrahydromyrcenol, thymol, triethyl citrate, 1,2,6-trihydroxyhexane, p-α,α- trimethylbenzyl alcohol, 2-(5,5,6-trimethylbicyclo [2.2.1]hept-2-ylcyclohexmlol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose.

13. A composition comprising the siloxane of claim 11.

14. The alcohol or carbonyl compound releasing siloxane of claim 10 wherein said siloxane releases a carbonyl compound.

15. The siloxane of claim 14 wherein the carbonyl compound released is selected from the group consisting of glucose pentaacetate, 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bornyl acetate, bornyl isovalerate, bornyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthatide, butyl 2-methytbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro -nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethyiphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3-epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate, ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexalactone, γ-hexalactone, 3-hexenyl acetate, cis-3-hexenyl 2-methylbutanoate, cis-3-hexenyl cis-3-hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methybutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobomyl acetate, isobomyl propionate, isobutyl acetate, isobutyl butyrate, isobutyl cinnamate, isobutyl hexanoate, isobutyl isobutyrate, isobutyl 2-methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-(1-propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutytl isovalerate, 3-methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3-(4-t-butylphenylpropylidene) anthranilate, methyl (methylthio)acetate, methyl 2-(methylthio)propionate, methyl myristate, methyl nonanoate, methyl octanoate, methyl palmitate, 4-(4-methyl-3-pentenyl)-3-cyclohexenylmethyl acetate, methyl 2-methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3-phenylpropan-2-yl acetate, methyl 3-phenylpropionate, methyl propionate, 2-methylpropyl phenylacetate, methyl phenylacetate, 2-methyl-3-phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate, δ-nonalactone, γ-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, octyl butyrate, octyl isobutyrate, octyl isovalerate, octyl octanoate, octyl propionate, oxacycloheptadec-10-en-2-one, ω-pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropionate, phenethyl octanoate, phenethyl phenylacetate, phenethyl propionate, phenoxyethyl propionate, 2-phenoxyethyl 2-methylpropionate, 3-phenyl-2-propenyl propionate, 3-phenylpropyl acetate, 2-phenylpropyl butyrate, 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, 6-nonalactone, tetrahydrofurfuryl acetate, tetrahydrofurfuryl butyrate, tetrahydrofurfuryl propionate, tetrahydrolinalyl acetate, 2,6,6,8-tetramethyl-tricyclo [5.3.1.0(1.5)]udecan-8-yl acetate, p-tolyl acetate, p-tolyl isobutyrate, p-tolyl phenylacetate, triacetin, tributyl acetylcitrate, tributyrin, tripropionin, 3,5,5-trimethylhexyl acetate, δ-undecalactone, γ-undecalactone, γ-valerolactone, vanillin acetate, vanillyl isobutyrate, 1-vinyl-2-(1-methylpropyl)cyclohexyl acetate, whiskey lactone, butyraldehyde, citronellal, decanal, cis-4-decenal, trans-4-decenal, 2,4-dimethyl-3-cyclohexen-1-carbaldehyde, 2,6-dimethyl-5-heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3-(p-isopropylphenyl)propionaldehyde, isovaleraldehyde, lauric aldehyde, 2-methylbutyraldehyde, 2-methyl-3-(p-isopropylphenyl)propionaldehyde, 2-methylpentanal, 4-(4-methyl-3-pentenyl)-3-cyclohexen-1-carbaldehyde, 4-methylphenylacetaldehyde, 3-(methylthio)butanal, 2-methyl4-(2,6,6-trimethyl-2-cyclohexen-1-yl)butanal, 2-methylundecanal, nonanal, cis-6-nonenal, octanal, phenylacetaldehyde, 2-phenyipropionaldehyde, 3-phenyipropionaldehyde, propionaldehyde, p-tolylacetaldehyde, tridecanal, 2,4,6-trimethyl-3-cyclohexen-1-carbatdehyde, 2,6,10-trimethyl-9-undecanal, 7-undecenal, 8-undecenal, 9-undecenal, 10-undecenal, valeraldehyde, acetanisole, 1'-acetonaphthone, 2'-acetonaphthone, acetone, acetophenone, 2-acetoxy-2,5-dimethyl-3(2H)furanone, 2-acetylcyclopentanone, 4-acetyl-1,1-dimethyl-6-t-butylindan, 7-acetyl-1,1,3,4,4,6-hexamethylindan, 2-acetyl-2-thiazoline, 6-acetyl-1,1,2,4,4,7-hexamethyl tetralin, allyl α-ionone, benzylideneacetone, 2,3-butanedione, 2-sec-butylcyclohexanone, 5-t-butyl-3,5-dinitro-2,6-dimethylacetophenone, butyrophenone, camphor, 2-decanone, 3-decanone, 3-decen-2-one, dihydrocarvone, dihydro-p-ionone, dihydrojasmone, 4,5-dihydro-3 (2H)-thiophenone, 2',4'-dimethytacetophenone, 3,4-dimethyl-1,2-cyclopentadione, 3,5-dimethyl-1,2-cyclopentadione, 2,6-dimethyl-4-heptanone, 1,3-diphenyl-2-propanone, 4-(1-ethoxyvinyl)-3,3,5,5-tetramethylcyclohexanone, p-ethylacetophenone, ethyl vinyl ketone, geranylacetone, 2,3-heptanedione, 2-heptanone, 3-heptanone, 4-heptanone, 3,4-hexanedione, 3-hexanone, 4-hexen-3-one, 2-hexylidene cyclopentanone, a-ionone, b-ionone, 4-isobutyt-2,6-dimethyl-3,5-dinitroacetophenone, isophorone, 6-isopropyldecahydro-2-naphthone, cis-j asmone, livescone, 4-methoxyacetophenone, 4-(p-methoxyphenyl)-2-butanone, 4'-methylacetophenone, 3-methyl-1,2-cyclohexanedione, 3-methyl-2-cyclohexen-l-one, 2-(2-(4-methyl-3-cylcohexen-1-yl) propyl)cyclopentanone, 3-methyl-2-cyclopenten-l-one, methyl dihydroj asmonate, methyl ethyl ketone, 2-methyl-3-heptanone, 5-methyl-2-hepten-4-one, 6-methyl-5-hepten-2-one, 5-methyl-α-ionone, 1-(2-methyl-5-isopropyl-2-cyclohexenyl)-1-propanone, 4-methyl-2-pentanone, 3-methyl-2-(2-pentenyl)-2-cyctopenten-1-one, 4-methyl-1-phenyl-2-pentanone, 2-methyltetrahydrofuran-3-one, 2-methyltetrahydrothiophen-3-one, 2-nonanone, 3-nonanone, 2-octanone, 3-octanone, 1-octen-3-one, 3-octen-2-one, 4-oxoisophorone, 2-pentadecanone, 2,3-pentanedione, 2-pentanone, 3-pentanone, 3-penten-2-one, 1-phenyl-1,2-propandione, propiophenone, pulegone, 2-tridecanone, 2,2,6-trimethylcyclohexanone, 4-(2,6,6-trimethyl-2-cyleohexen-1-yl)-3-methyl-3-buten-2-one, 2-undecanorte, and 6-undecanone.

16. A composition comprising the siloxane of claim 14.
17. A composition comprising the siloxane of claim 10.
18. A hydrolyzed product of the alcohol or carbonyl compound releasing siloxane of claim 1, wherein the oxygen-bound Frag radical is released from said siloxane and said oxygen is converted to an OH-moiety.
19. A composition comprising the siloxane of claim 1.
20. An article of manufacture comprising the siloxane of claim 1.
21. A composition consisting essentially of the siloxane of claim 1.

* * * * *